United States Patent [19]

Hosobuchi et al.

[11] Patent Number: 4,684,624

[45] Date of Patent: Aug. 4, 1987

[54] METHOD OF TREATING CEREBRAL ISCHEMIA

[75] Inventors: Yoshio Hosobuchi, 116 Kinross Dr., San Rafael, Calif. 94901; Nancy M. Lee, 1830 Funston Ave.; Horace H. Loh, 54 Mendosa, both of San Francisco, Calif. 94116; Jaw-Kang Chang, 90 Curtis Ct., San Carlos, Calif. 94070

[73] Assignees: Yoshio Hosobuchi, San Rafael; Nancy M. Lee; Horace H. Loh, both of San Francisco; Jaw-Kang Chang, San Carlos, all of Calif.

[21] Appl. No.: 735,948

[22] Filed: May 20, 1985

Related U.S. Application Data

[63] Continuation of Ser. No. 564,741, Dec. 22, 1983, abandoned.

[51] Int. Cl.⁴ ............................................. A61K 37/02
[52] U.S. Cl. ...................................... 514/15; 514/14; 514/809
[58] Field of Search ........................... 514/809, 14, 15

[56] References Cited

U.S. PATENT DOCUMENTS

| | | | |
|---|---|---|---|
| 2,149,007 | 4/1979 | Buckler et al. | 560/53 |
| 3,952,006 | 4/1976 | Tahara et al. | 260/309 |
| 3,985,758 | 10/1976 | Murakami et al. | 260/295.5 R |
| 4,256,883 | 3/1981 | Nicolaou et al. | 544/235 |
| 4,267,182 | 5/1981 | Holaday et al. | 424/260 |
| 4,280,494 | 7/1981 | Cosgrove, Jr. et al. | 128/213 R |
| 4,351,337 | 9/1982 | Sidman | 128/260 |
| 4,361,553 | 11/1982 | Loh et al. | 514/15 |
| 4,364,951 | 12/1982 | Skuballa et al. | 424/263 |
| 4,394,385 | 7/1983 | Cragoe | 424/285 |
| 4,399,129 | 8/1983 | Gowers et al. | 424/244 |
| 4,464,358 | 8/1984 | Cox | 514/18 |

OTHER PUBLICATIONS

Kiang et al., *Exp. Ther.* (1983), "Tolerance to Morphine Bradycardia in the Rat".
Wei et al., *Life Sciences*, vol. 26, pp. 1517–1522, (1980), "Cardiovascular Effects of Peptides Related to the Enkephalins and Casomorphin".
Kiang et al., *Amer. Soc. Phar. Exp. Thera.*, 1982 FASEB Abstract Form, "Tolerance Development to Morphine Bradycardia in the Rat and Its Modification by Dynorphin (1-13) and Leucine-Enkephalin".
Sapru et al., *Jour. Phar. & Exp. Ther.* 217:228–234 (1981), "Stimulation of Pulmonary J Receptors by an Enkephalin-Analog".
Baskin & Hosobuchi, "Naloxone Reversal of Ischaemic Neurological Deficits in Man," *Lancet* 2:272–275 (1981).
Hosobuchi et al., "Reversal of Induced Ischemic Neurologic Deficit in Gerbils by the Opiate Antagonist Naloxone," *Science*, 215:69–71 (1982).
Levy et al., "Failure of Naloxone to Limit Clinical or Morphological Brain Damage in Gerbils with Unilateral Carotid Artery Occlusion," *Abstracts of the 12th Annual Meeting of the Society for Neuroscience*, p. 248 (1982).
Holaday & D'Amato, "Naloxone or TRH Fails to Improve Neurologic Deficits in Gerbil Models of 'Stroke'", *Life Science*, 31:385–392, (1982).
Imura et al., *Ann. Rev. Physiol.* 43:265–278 (1981).
Viveros et al., *Adv. Biochem. Psychopharmacol*, 221 191–204 (1980).
Lang et al., *Life Sci.*, 32:399–406 (1983).
Elde et al., *Neuroscience* 1:349–357 (1976).
Polak et al., *Lancet* 1:972–974 (1977).
Alumets et al., *Histochem* 56: 187–196 (1978).
Woo et al., *Life Sciences* 31:1817–1882 (1982).
O'Brien & Waltz, "Transorbital Approach for Occluding the Middle Cerebral Artery Without Craniectomy," *Stroke* 4: 201–206 (1973).
*Science*, vol. 218, pp. 592–593. Nov. 5, 1982, "Naloxone and Ischemic Neurologic Deficits in the Gerbil: Is There an Effect?", Holaday & D'Amato.
*Science*, vol. 218, p. 594, Commentary on Letter, Hosobuchi & Baskin.
Chem Abstracts Citation of Hosobuchi et al., vol. 97, 174869h in Adv. Endog. Exog. Opioids, Proc. Int. Narc. Res. Conf. 12th (1982).
*Nature*, vol. 312, Dec. 6, 1984, "Dynorphin(1-13) Improves Survival in Cats with Focal Cerebral Ischaemia", Baskin et al.
*Life Sciences*, vol. 31, pp. 2201–2204, (1982), "Naloxone Reversal of Ischemic Neurologic Deficits in Baboons is not Mediated by Systemic Effects", Baskin et al.
*Life Sciences*, vol. 31, pp. 2205–2208, "Effect of Naloxone on Neurologic Deficit & Cortical Blood Flow During Focal Cerebral Ischemia in Cats", Levy et al. (1982).

*Primary Examiner*—Johnnie R. Brown
*Assistant Examiner*—Jacqueline M. Stone
*Attorney, Agent, or Firm*—Majestic, Gallagher, Parsons & Siebert

[57] ABSTRACT

A method of treatment for patients suffering from cerebral ischemia is provided by administering an opioid peptide. Particulary preferred is the administration of dynorphin, or dynorphin-related peptides, in the acid or amidated form. Practice of the invention is useful in prolonging survival.

8 Claims, No Drawings

METHOD OF TREATING CEREBRAL ISCHEMIA

This is a continuation of application Ser. No. 564,741, filed Dec. 22, 1983, now abandoned.

FIELD OF THE INVENTION

The present invention generally relates to a method of treating ischemia with an opioid peptide, and more particularly to the use of dynorphin in reversing neurologic deficits and in prolonging survival following cerebral ischemia.

BACKGROUND OF THE INVENTION

While many infectious diseases have been controlled or eliminated by medical science, chronic diseases—such as heart attack, stroke and cancer—have emerged as major causes of death. Where death does not result from stroke, the victim is often seriously disabled. The death rate for stroke victims is over 2 per 1,000 in the United States. The Japanese, while having one of the lowest incidences of death from heart disease, have one of the highest from strokes.

Various different compounds have been suggested as useful for the treatment of stroke. For example, it appears that aspirin may reduce the risk of transient ischemic attacks, or small strokes, and deaths from stroke. U.S. Pat. No. 4,256,883, inventors Nicolaou et al., issued Mar. 17, 1981, discloses prostacyclin analogs said to be useful in vascular constrictions and in cerebral strokes associated with essential hypertension. U.S. Pat. No. 4,364,951, inventors Skuballa et al., issued Dec. 21, 1982, discloses prostacyclins said to possess properties useful, inter alia, in treating stroke. U.S. Pat. No. 4,394,385, inventor Cragoe, issued July 19, 1983, discloses the use of benzofuranyloxyacetic acids and anti-inflammatory steroids said to be useful in controlling edema from ischemic stroke.

It has been recently reported that the opiate antagonist naloxone can reverse neurologic deficits secondary to cerebral ischemia, whereas morphine exacerbates them. Baskin and Hosobuchi, "Naloxone reversal of ischaemic neurological deficits in man," *Lancet* 2:272–275 (1981). It has also been reported that neurologic deficits produced by unilateral carotid ligation in gerbils can be reversed by the intraperitoneal administration of naloxone. Hosobuchi et al., "Reversal of induced ischemic neurologic deficit in gerbils by the opiate antagonist naloxone," *Science* 215:69–71 (1982).

However, Levy, et al. have reported that treatment with naloxone did not produce improved neurologic function or alter infarct size in gerbils that had undergone temporary carotid occlusion. ("Failure of naloxone to limit clinical or morphological brain damage in gerbils with unilateral carotid artery occlusion," *Abstracts of the 12th Annual Meeting of the Society for Neuroscience,* p. 248 (1982).) Similarly, Holaday and D'Amato reported that naloxone had no beneficial effect on either survival or neurologic function in several different models of stroke in gerbils. ("Naloxone or TRH fails to improve neurologic deficits in gerbil models of 'stroke'," *Life Science* 31:385–392 (1982).)

SUMMARY OF THE INVENTION

It is an object of the present invention to provide a method of treatment for patients suffering from ischemia, such as acute or non-acute cerebral ischemia.

In one aspect of the present invention, a method of treating a patient suffering from cerebral ischemia comprises administering to the patient a therapeutically effective dose of an opioid peptide following the cerebral ischemia. Subsequent doses are then preferably delivered to the patient. Particularly preferred opioid peptides are dynorphin(1-13) and dynorphin(1-10) amide. Practice of the present invention with patients suffering from acute focal cerebral ischemia is useful in prolonging survival, and is believed to be useful in partially reversing neurologic deficits resulting from cerebral ischemia.

BEST MODE OF PRACTICING THE INVENTION

Since the discovery of opiate receptors within the central nervous system, it has been believed that endogenous opiate ligands may be involved in the central nervous system function in both health and disease states. Investigative attention has focused primarily on the role of these substances in the modulation of the perception of painful stimuli, but they have also been implicated in pituitary function, seizure disorders and mental illness.

Opioid peptides are found in the circulatory system, presumably from sources in the pituitary (Imura et al., *Ann Rev. Physiol.* 43: 265–278 (1981)), adrenal medulla (Viveros et al, *Adv. Biochem. Psychopharmacol.* 22: 191–204 (1980)), heart (Lang et al., *Life Sci.* 32: 399–406 (1983)), and gut (Elde et al., *Neuroscience* 1: 349–357 (1976); Polak et al., *Lancet* 1: 972–974 (1977); Alumets et al., *Histochem* 56: 187–196 (1978)).

A prevailing theory is that most actions of opioid drugs are within the central nervous system (that is, inside the brain or spinal cord). However, evidence that endogenous opioid peptides appear to condition the sensitivity of the peripheral nerves to stimuli that affect heart rate and blood pressure has been found, and it is believed that circulating opioid peptides, under normal conditions, are operating to control the sensitivity of these peripheral sites of the autonomic nervous system to such endogenous substances.

Endogenous opioid peptides can be grouped into three classes: β-endorphin and certain related compounds; the enkephalins, which are the smallest opioid peptides; and dynorphin, α-neo-dynorphin and their related peptides. Of the three types, β-endorphin seems to be the one most closely associated with morphine-like effects. Administration of this peptide intracerebroventricularly (i.c.v.) induces analgesia with both tolerance and physical dependence developing after prolonged treatment; moreover, cross-tolerance and cross-dependence are observed in relationship to morphine. In contrast, administration of the natural enkephalins, leucine-(leu) and methionine-(met) enkephalin has been reported to have very weak or no analgesic activity when given i.c.v.

Dynorphin was first isolated from pituitary glands, and the sequence of its first 13 N-terminal amino acids determined; this fragment has been synthesized and its properties studied along with that of the natural compound's full 17 amino acid sequence. The first 13 amino acids of dynorphin, or dynorphin(1-13), have the sequence:

TYR—GLY—GLY—PHE—LEU—ARG—ARG—ILE—
 1      2      3      4      5      6      7      8

-continued

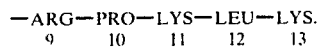

The N-terminal end contains Leu-enkephalin (those amino acids numbered 1-5), followed by the C-terminal extension (those amino acids numbered 6-13). The inclusion of Leu-enkephalin has been believed to be necessary as a biological "homing device" for activity, and the length of extension beyond Leu-enkephalin has been believed to be critical for its potency.

Dynorphin has little or no analgesic potency in mice. While this lack of effect was originally ascribed to rapid degradation of dynorphin in the brain, it has been shown that dynorphin exhibited other pharmacological effects, indicating it should remain intact long enough to produce analgesia. Thus, U.S. Pat. No. 4,361,553, inventors Loh et al., issued Nov. 30, 1982, discloses that although dynorphin inhibits, or antagonizes, the analgesic response to both morphine and $\beta$-endorphin it has the opposite effect in tolerant animals. That is, dynorphin potentiates the analgetic effect of both morphine and $\beta$-endorphin in morphine-tolerant animals. Dynorphin thus behaves as neither a classical agonist nor an antagonist.

It has recently been reported that dynorphin(1-10) amide does not antagonize narcotic analgesics in naive animals (as does dynorphin(1-17) and dynorphin(1-13), although it does potentiate the analgesic effect in tolerant hosts. Woo, et al., *Life Sciences* 31:1817–1882 (1982).

By contrast to the in vivo opioid properties of an opioid peptide such as dynorphin, naloxone (17-allyl-4-5α-epoxy-3,14-dihydroxymorphinan-6-one) behaves as a "classic" narcotic antagonist. Other non-peptide narcotics include naltrexone, nalorphine, diprenorphine, lavallorphan, pentazocine, metazocine, cyclazocine, and etazocine.

The present invention provides a method for treating patients suffering from cerebral ischemia by administration of an opioid peptide. Suitable opioid peptides in accordance with the present invention include dynorphin, dynorphin analogs, and dynorphin amide analogs.

Preferred opioid peptides for practice of the present invention are those polypeptides having the amino acid sequence TYR-GLY-GLY-PHE-LEU-ARG-ARG-$AA^8$-$AA^9$-$AA^{10}$-$(AA^{11})_w$, wherein $AA^8$ is TYR, ILE, LEU or LYS, $AA^9$ is ARG or PRO, $AA^{10}$ is PRO or LYS, $AA^{11}$ is LYS, LYS-LEU or LYS-LEU-LYS, w is 0 or 1, and with the polypeptide being in acid or amidated form. Two particularly preferred embodiments for practice of the present invention are dynorphin(1-13) and dynorphin(1-10) amide.

Preparation of suitable dynorphin and dynorphin-related peptides for practice of the present invention may be by methods and apparatus known to the art for peptide synthesis, with Example I, below (preparation of dynorphin(1-10) amide) being illustrative.

EXAMPLE I

Dynorphin(1-10)-$NH_2$ was synthesized on a solid support of Boc-Pro-BHA (Benzyhydrylamine) resin (2 mM/4.5 g of resin). With the Merrifield procedure on a Peninsula manual solid-phase peptide synthesizer, the corresponding Boc-protected amino acids were added respectively onto the Boc-Pro-BHA resin: Arg(Tos), Ile, Arg(Tos), Arg(Tos), Leu, Phe, Gly, Gly and Tyr(o-Br-Z). A 5.0 molar excess of each protected amino acid was used. The success of the coupling reaction was monitored by the semi-quantitative ninhydrin test. The following steps were employed to couple the Boc-protected amino acid to Boc-Pro-BHA resin:

(1) Washing with $CH_2Cl_2$ (3×100 ml)
(2) Prewashing with 33% TFA in $CH_2Cl_2$ with 1% indole (1×100 ml)
(3) Deprotection with 33% TFA in $CH_2Cl_2$ with 1% indole (1×100 ml), 20 min.
(4) Washing with $CH_2Cl_2$ (1×100 ml)
(5) Washing with EtOH (1×100 ml)
(6) Washing with $CH_2Cl_2$ (2×100 ml)
(7) Prewashing with 10% $Et_3N$ in $CH_2Cl_2$ (1×100 ml)
(8) Neutralization with 10% $Et_3N$ in $CH_2Cl_2$ (1×100 ml), 10 min.
(9) Washing with $CH_2Cl_2$ (3×100 ml)
(10) Protected amino acid (5.0 molar excess) in DMF (10 ml) and $CH_2Cl_2$ (50 ml) was added
(11) DCC in $CH_2Cl_2$ (0.5M, 20 ml) was added and the reaction time was up to three hours
(12) Washing with $CH_2Cl_2$ (3×100 ml)

The resulting protected Boc-Tyr(O-Br-Z)-Gly-Gly-Phe-Leu-Arg(Tos)-Arg(Tos)-Ile-Arg(Tos)-Pro-BHA resin was washed well with 33% TFA in $CH_2Cl_2$, $CH_2Cl_2$ and MeOH respectively. After drying in vacuo overnight, the peptide resin was cleaved by HF (30 ml/g of resin) in the presence of anisole (3 ml/g of resin) for one hour at 0° C. The reaction mixture was dried in vacuo and washed with anhydrous ether. The desired peptide was dissolved in 10% HOAc and the resin was filtered off. The filtrate was lyophilized to give crude dynorphin(1-10)-$NH_2$. This peptide was purified by partition chromatography using n-BuOH:pyridine:$H_2O$ (11:5:3) as eluting solvent and CM ion-exchange chromatography to afford the pure dynorphin(1-10)-$NH_2$.

It is believed that factors affecting response to therapy for cerebral ischemia in accordance with the present invention include the dosage, the route of administration, and duration of therapy.

However, blood pressure does not appear to be a factor affecting response to therapy for cerebral ischemia in accordance with the present invention, as blood pressure monitering during practice of the invention has shown no changes in cardiac output, systemic blood pressure or cerebral blood flow.

In treating patients suffering from acute focal cerebral ischemia in accordance with the present invention, therapy is initiated by administering a dose of suitable opioid peptide and then preferably continued by administering subsequent doses.

The initial dose may be from about 1.0 μg/kg of patient's weight to about 10 mg/kg of patient's weight, more preferably about 100 μg/kg of patient's weight, and can be delivered by various means known to the art, such as by intravenous injection ("I.V."). Subsequent doses may also be delivered by various means known to the art, such as by injections or through topical applications in conjunction with a drug carrier such as dimethyl sulfoxide or Azone (available from Nelson Laboratories). However, it is preferred that the subsequent doses be delivered substantially continuously for as long as the patient is in a life threatening situation, or until the patient's condition stabilizes, and be at a rate between about 0.01 μg/hr to about 100 μg/hr. For example, continuous infusion may be by use of an implanted mini-pump, or by I.V. When the patient's condition stabilizes, then the doses may be gradually reduced, or titrated. Depending upon the mode of administration, the opioid peptide may be formulated with a wide variety of physiologically acceptable carriers, such as aqueous saline and phosphate buffered saline, and may include physiologically acceptable excipients, such as glucose, mannitol, or the like.

The following experimental methods, materials and results are described for purposes of illustrating the present invention. However, other aspects, advantages and modifications within the scope of the invention will be apparent to those skilled in the art to which the invention pertains.

EXPERIMENTAL

On the basis of a random number table, adult male cats were assigned to one of six groups to be treated with: (1) saline (12 cats), (2) naloxone (13 cats), (3) naltrexone (10 cats), (4) diprenorphine (13 cats), (5) dynorphin (1-13) (10 cats), and (6) dynorphin(1-10) amide (5 cats). The cats were sedated with 50 mg of ketamine administered intramuscularly. Anesthesia was induced by admixture of halothane, nitrous oxide, and oxygen administered by mask. The trachea was then intubated but the cat was allowed to breath spontaneously. One million units of penicillin G were then administered intramuscularly and the cats were placed in a stereotactic apparatus. Transorbital occlusion of the right middle cerebral artery (MCA) was performed using the technique in cats first described by O'Brien and Waltz. ("Transorbital approach for occluding the middle cerebral artery without craniectomy," Stroke 4: 201-206 (1973).)

An incision was made in the supraorbital region using aseptic technique, and dissection was performed in a subperiosteal plane along the roof of the orbit. The globe was incised and the contents removed. The ciliary arteries and ophthalmic vessels were coagulated with bipolar coagulating forceps under magnification of the surgical microscope. Straight and curved microscissors were used to complete the orbital dissection and the orbital contents were evacuated. A microsurgical drill was used to remove the optic strut, thus enlarging the optic foramen. The dura was incised and the carotid bifurcation was exposed. An arachnoid dissection was formed to free the internal carotid, middle cerebral, posterior communication, and anterior cerebral arteries. The segment of the MCA proximal to the lenticulostriate arteries (MI) was coagulated with the bipolar forceps and transected with microscissors. The orbit was irrigated and filled with dental cement to prevent leakage of CSF. The wound was sutured closed and colloidin spray was applied as a dressing.

A small incision was made in the midline in the lumbar region and a subcutaneous pocket was created for the later placement of an osmotic pump that was designed to deliver drug at a constant volume. This incision was sutured loosely using a running stitch. The cat was allowed to awaken and was examined 6 hours following MCA occlusion. Neurologic function was assessed independently by two individuals who were unaware of the experimental protocol.

In a blind study, the cats then received an intraperitoneal injection of one of the following solutions: 2 ml of sterile normal saline; 2 ml of a 10 mg/kg solution of naloxone dissolved in sterile normal saline; 2 ml of a solution containing 500 µg of diprenorphine dissolved in sterile normal saline; 2 ml of a solution containing 10 mg/kg of naltrexone dissolved in sterile normal saline; 2 ml of a solution containing 10 mg/kg of dynorphin(1-13) dissolved in sterile normal saline; and, 2 ml of a solution containing 10 mg/kg of dynorphin(1-10) amide dissolved in sterile, normal saline. A second neurologic asssessment was performed 20 minutes later.

The cats were then sedated with 50 mg of ketamine administered intramuscularly and using sterile technique, an osmotic pump (available from ALZA Corp., Palo Alto, CA) was implanted in the previously created subcutaneous pocket in the lumbar region to deliver either saline at 10 µl/hr, diprenorphine at 100 µg/hr, naloxone at 5 mg/kg/hr, naltrexone at 1 mg/kg/hr, 50 µg/hr dynorphin(1-13) or 50 µg/hr dynorphin(1-10) amide. Again, the investigators were not aware as to which treatment was being administered.

Neurologic assessments were performed daily for as long as the cats were alive, or until 7 days had elapsed. One million units of penicillin G were administered intramuscularly daily and subcutaneous injections of sufficient lactated Ringer's solution provided adequate daily fluid maintenance. Once a cat began to eat or drink, subcutaneous fluids were discontinued. If a cat was found dead, a craniectomy was performed, the brain removed, and a coronal section was made at the level of optic chiasm. After 7 days had elapsed the surviving cats were sacrificed.

The coronal sections were incubated in a 2% solution of 2,3,5 triphenyltetrazolium chloride (TTC) for 25 minutes. TTC has been used extensively to demonstrate the presence and extent of acute myocardial infarcts, and gives a vivid indication of cerebral infarction in the acute state. The reaction product of TTC and viable tissue is a deep red formazan that deeply stains normal gray matter, whereas normal white matter stains with lesser intensity. Infarcted tissue does not stain.

Color slides were made of the stained brains. A neuropathologist who was unaware of the experimental protocol made tracings of the entire affected hemisphere and infarcted area from projected images of the slide. Using a digitizer, the percentage of infarcted tissue relative to the entire hemisphere was calculated for both sections in each cat; this defined the infarct size.

Table I, below illustrates the mortality for each group as a function of time following the cerebral artery occulusions.

TABLE I

|  | less than 24 hours | 24-28 hours | 48-72 hours | lived up to 7 days |
|---|---|---|---|---|
| Saline | 100% | 0% | 0% | 0% |
| Diprenorphine | 84% | 8% | 8% | 0% |
| Naloxone | 54% | 15% | 0% | 31% |
| Naltrexone | 40% | 10% | 10% | 40% |
| Dynorphin (1-10) amide | 80% | 0% | 0% | 20% |
| Dynorphin (1-13) | 20% | 20% | 0% | 60% |

As illustrated by the data of Table I above, all cats of the control, or saline group died in less than 24 hours. The administration of diprenorphine had little effect in prolonging survival. Both naloxone and naltrexone prolonged survival. Dynorphin(1-13) prolonged survival best of all the groups. Although the mortality rate results for dynorphin(1-10) amide in prolonging survival appear less impressive than for naloxone, naltrexone and dynorphin(1-13), the conditions of survival were of high quality and clinically quite significant.

The infarct size was not altered by any treatment administered and there was substantial similarity in the results among groups. That is, there was no statistically significant difference in infarct size among the groups.

While the invention has been described in connection with specific embodiments thereof, it will be understood that it is capable of further modification, and this application is intended to cover any variations, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A method of treating a patient suffering from cerebral ischemia comprising:

administering a therapeutically effective amount of an opioid peptide to the patient, the opioid peptide having the amino acid sequence TYR-GLU-GLY-PHE-LEU-ARG-ARG-$AA^8$-$AA^9$-$AA^{10}$-$(AA^{11})_w$, wherein $AA^8$ is TYR, ILE, LEU OR LYS, $AA^9$ is ARG or PRO, $AA^{10}$ is PRO or LYS, $AA^{11}$ is LYS, LYS-LEU or LYS-LEU-LYS, w is 0 or 1, and said opioid peptide is in acid or amidated form.

2. The method as in claim 1 wherein the opioid peptide is dynorphin(1-13) or dynorphin(1-10) amide.

3. The method as in claims 1 or 2 wherein an initial dose from about 1 µg/kg of patient's weight to about 10 mg/kg of patient's weight is administered.

4. The method as in claim 3 wherein subsequent doses of the opioid peptide are delivered to the patient for as long as the patient is in a life threatening situation or until the patient's condition stabilizes.

5. The method as in claim 4 wherein the subsequent doses are delivered substantially continuously at a rate between about 0.01 µg/hour to about 100 µg/hour.

6. A method of prolonging survival of a patient suffering from acute focal cerebral ischemia comprising:

administering to the patient an initial dose of dynorphin in an acid or amidated form following the cerebral ischemia, the dynorphin having the amino acid sequence TYR-GLY-GLY-PHE-LEU-ARG-ARG-ILE-ARG-PRO-$(AA^{11})_w$, wherein $AA^{11}$ is LYS, LYS-LEU or LYS-LEU-LYS, and w is 0 or 1, the initial dose being from about 1.0 µk/kg of patient's weight to about 10 mg/kg of patient's weight, and then continuing to deliver subseqent doses of dynorphin to said patient, the subsequent doses being delivered for as long as the patient is in a life threatening situation or until the patient's condition stabilizes.

7. The method as in claim 6 wherein the subsequent doses are delivered substantially continuously at a rate between about 0.01 µg/hour to about 100 µg/hour.

8. The method as in claim 6 wherein the subsequent doses are delivered by infusion.

* * * * *

UNITED STATES PATENT AND TRADEMARK OFFICE
CERTIFICATE OF CORRECTION

PATENT NO. : 4,684,624

DATED : Aug. 4, 1987

INVENTOR(S) : Hosobuchi et al.

It is certified that error appears in the above-identified patent and that said Letters Patent is hereby corrected as shown below:

Col. 7, line 23: "TYR-GLU-GLY'" should be --TYR-GLY-GLY- --;

and line 25: "OR" should be --or--.

Signed and Sealed this

Fifth Day of January, 1988

Attest:

DONALD J. QUIGG

Attesting Officer

Commissioner of Patents and Trademarks